United States Patent [19]

Nagel et al.

[11] Patent Number: 5,374,546
[45] Date of Patent: Dec. 20, 1994

[54] PROCESS FOR STABILIZING 1-METHYLHYDANTOINASE, USE AND METHOD OF IT FOR DETERMINING AN ANALYTE AND AGENTS SUITABLE FOR THIS

[75] Inventors: Rolf Nagel, Bürstadt; Ulfert Deneke, Rimbach-Zotzenbach; Jürgen Mistele, Mannheim, all of Germany

[73] Assignee: Boehringer Mannheim GmbH, Mannheim, Germany

[21] Appl. No.: 822,176

[22] Filed: Jan. 16, 1992

[30] Foreign Application Priority Data

Feb. 2, 1991 [DE] Germany ............... 4103220

[51] Int. Cl.$^5$ .............. C12N 9/96; C12N 9/78
[52] U.S. Cl. .................... 435/188; 435/18; 435/29; 435/227
[58] Field of Search ....... 422/61; 435/18, 29, 435/188, 227

[56] References Cited

U.S. PATENT DOCUMENTS

| | | | |
|---|---|---|---|
| 3,133,001 | 5/1964 | Muset | 435/188 |
| 3,325,364 | 6/1967 | Merritt et al. | 435/188 X |
| 3,413,198 | 11/1968 | Deutsch | 435/188 X |
| 3,539,450 | 11/1970 | Deutsch | 435/188 |
| 4,230,664 | 10/1980 | Cais | 422/61 |
| 4,331,761 | 5/1982 | Dawson et al. | 435/188 |
| 4,400,464 | 8/1983 | Vormbreck et al. | 435/188 X |
| 4,465,770 | 8/1984 | Modnovich | 435/188 X |
| 4,645,739 | 2/1987 | Deeg et al. | 435/25 |
| 4,816,393 | 3/1989 | Siedel et al. | 435/18 |
| 4,876,067 | 10/1989 | Deneke et al. | 422/56 |
| 4,888,289 | 12/1989 | Takami et al. | 435/188 X |
| 4,912,037 | 3/1990 | Lemonnier | 435/29 X |
| 5,047,329 | 9/1991 | Suzuki | 435/18 |

OTHER PUBLICATIONS

Brown et al., "Role of Metal Cofactors in Enzyme Regulation. Differences in the Regulatory . . . ", Biochemistry 1981, 20, 2503-2512.
Fukushima et al., "Binding of Divalent Cation to Phosphoenzyme of Sodium—and Potassium–transport ATP.", J. Biol Chem, 253 (19), 1978; 6853-6867.
Seidel, Analytical Letters, 21(6), 1009-1017 (1988).
Kim et al., Biochemical and Biophysical Research Communications, pp. 1006-1012.
Enzyme Handbook, vol. II, pp. 501, 689, 690.

Primary Examiner—Donald E. Czaja
Assistant Examiner—Milton I. Cano
Attorney, Agent, or Firm—Felfe & Lynch

[57] ABSTRACT

The invention concerns a process for stabilizing the enzyme 1-methylhydantoinase (NMHase) which is characterized in that the NMHase is treated with divalent metal ions, a nucleoside triphosphate and a complexing agent which complexes these divalent metal ions. In addition the invention concerns the use of an enzyme stabilized in this way in a method for the determination of an analyte in which 1-methylhydantoin is converted, as well as a corresponding reagent.

18 Claims, 2 Drawing Sheets

PROCESS FOR STABILIZING 1-METHYLHYDANTOINASE, USE AND METHOD OF IT FOR DETERMINING AN ANALYTE AND AGENTS SUITABLE FOR THIS

FIELD OF THE INVENTION

The invention concerns a process for the stabilization of 1-methylhydantoinase, the use of a stabilized 1-methylhydantoinase for the determination of an analyte such as e.g. creatinine, a corresponding method of determination as well as agents which are suitable for this.

BACKGROUND AND PRIOR ART

In analytical chemistry, in particular in clinical chemical diagnostics, there is a continuously increasing demand for enzymatic methods for the determination of natural products, biological metabolic products and compounds derived therefrom. The reasons are the extraordinarily high specificity of enzyme-catalyzed substance conversions, their rapid and defined course which is free from losses under mild reaction conditions—usually between 15° and 40° C. in aqueous media in a neutral pH range—as well as the possibility of determining these quantitatively in a simple and sensitive manner, in particular using photometric measurement procedures either directly or with the aid of coupled indicator reactions.

An enzymatic method of determination is also particularly valuable for the determination of creatinine, a component of serum and urine that is important for kidney diagnosis, which can be converted in an enzymatic reaction which has been known for a long time into 1-methylhydantoin (N-methylhydantoin, NMH) and ammonia by means of creatinine iminohydrolase (E.C. 3.5.4.21).

Several methods are already known for the enzymatic determination of creatinine in serum or urine (Wahlefeld, A. W.; G. Holz and H. U. Bergmeyer, in H. U. Bergmeyer: Methoden der enzymatischen Analyse, Third Edition, Volume II, Verlag Chemie, Weinheim 1974, p. 1834–1838; Fossati, P.; L. Prencipe, and G. Berti, Clinical Chemistry 29, 1494–1496 (1983); Tanganelli, E.; L. Prencipe; D. Bassi; S. Cambiaghi, and E. Murador, Clinical Chemistry 28, 1461–1464 (1983); however, they all have the disadvantage that they either proceed via creatine (Wahlefeld et al.; Fossati et al.) or via ammonia (Tanganelli et al.) as intermediate products in the reaction sequence. These are substances which are present in the serum or urine sample to be analyzed in varying concentrations which are quite substantial compared to creatinine. Thus in order to determine creatinine in these cases, it is necessary to carry out differential measurements on two separate or successive reaction mixtures, one in which first the free creatine or ammonia is determined and a second in which the portion of additional creatine or ammonia formed from creatinine is determined ("sample/sample blank method" or "$A_1/A_2$ method") by addition of either creatinine amidohydrolase (E.C. 3.5.2.10) or creatinine iminohydrolase (=creatinine deiminase).

Such methods are relatively complicated for a manual procedure and their application to automated analytical systems is also very limited, in particular when longer incubation periods are necessary for the completion of the conversion reactions. In principle it is possible to carry out the creatinine determination with the so-called kinetic "fixed-time" method by suitable choice of reaction conditions using the known enzymatic methods and thus obviating the sample blank measurement; this, however, requires very strict adhesion to the measurement times under defined temperature conditions which is only possible with an adequate precision on automated analyzers and conversely virtually excludes manual application.

A new enzymatic method for the determination of creatinine or 1-methylhydantoin is described in U.S. Pat. No. 4,816,393. The substance 1-methylhydantoin is hydrolyzed to N-carbamoylsarcosine using the enzyme 1-methylhydantoinase (NMHase) which requires a nucleoside triphosphate, preferably ATP, as well as divalent metal ions and in some circumstances $K^+$ ions and/or $NH_4$ ions for its activity. This enzyme is also described in H. Yamada et al., FEBS Microbiol. Letters 30, 337–340 (1985), in S. Shimizu et al., Arch. Microbiol. 145, 322–328 (1986) and in Shimizu et al., Biochem. Biophys. Res. Comm. 142, 1006–1012 (1987).

It is available for example from Arthrobact. spec., Micrococcus spec., Moraxella spec., or Brevibacterium spec.

In a preferred variant of the test N-carbamoylsarcosine amidohydrolase (E.C. 3.5.3.59) known from U.S. Pat. No. 4,645,739 converts N-carbamoylsarcosine to sarcosine which can then, together with e.g. sarcosine oxidase (E.C. 1.5.3.1) and peroxidase (E.C. 1.11.1.7), be detected photometrically, e.g. by a suitable redox indicator: creatinine + $H_2O$ → 1-methylhydantoin + $NH_3$ 1-methylhydantoin + ATP + $2H_2O$ → N-carbamoylsarcosine + ADP + $P_i$ N-carbamoylsarcosine + $H_2O$ → sarcosine + $NH_3$ + $CO_2$ sarcosine + $O_2$ + $H_2O$ → $H_2O_2$ + formaldehyde + glycine $H_2O_2$ + redox indicator (red.) → $H_2O$ + redox indicator (ox.)

A corresponding photometric method for the determination of creatinine is also described in J. Siedel et al., Anal. Letters 21, 1009–1017 (1988).

Endogenous substances present in body fluids should not interfere with this creatinine or 1-methylhydantoin determination since 1-methylhydantoin and the reaction products of the subsequent indicator reaction are not natural components of serum or urine. Therefore a sample blank measurement should not be necessary.

However, it has turned out that the use of NMHase for creatinine determination is limited by two disadvantageous enzyme properties. NMHase requires enzyme-bound 1-methylhydantoin for its stability (ca. 2 –2.5 μmol/KU, U=international unit), i.e. it is stabilized by its own substrate. In general 1-methylhydantoin remains bound-to the enzyme during enzyme purification. However, in the presence of a nucleoside triphosphate and divalent metal ions, such as $Mg^{2+}$, as for example in a method for determining creatinine it is completely degraded enzymatically and causes a blank reaction similar to an endogenous substrate.

This blank reaction is especially disadvantageous in a determination method in which the amount of NMHase used in the test can vary widely, which can be the case for example in a carrier-bound test. Since the blank reaction caused by enzyme-bound NMH depends, on the one hand on the amount of NMHase used and on the other hand also on the varying NMH content of the NMHase itself, it is also necessary to always determine the blank reaction separately for such a test and this blank value has to be subtracted from the measured value.

On the other hand the NMHase is very unstable without enzyme-bound substrate and cannot be used for enzymatic methods of determination such as e.g. creatinine determination. In addition it was found that the nucleoside triphosphate necessary for the enzymatic reaction of NMHase is only of limited stability in the presence of NMHase since an NMHase shows ATPase activity and degrades ATP over the course of time.

The object of the present invention was therefore to provide a process which stabilizes NMHase in such a way that a stable enzyme is provided even in the absence of enzyme-bound 1-methylhydantoin or other substrate analogues and to provide an improved and more exact method for the determination of creatinine or other analytes which can be detected by means of a reaction catalyzed by NMHase.

This object is achieved according to the present invention by the measures as described in the claims.

SUMMARY OF THE INVENTION

Surprisingly it turned out that NMHase can be stabilized, even in the absence of enzyme-bound substrate, by using a complexing agent which complexes divalent metal ions acting as cofactors that are used in the NMHase reaction.

DETAILED DESCRIPTION OF PREFERRED EMBODIMENTS

Figure 1:
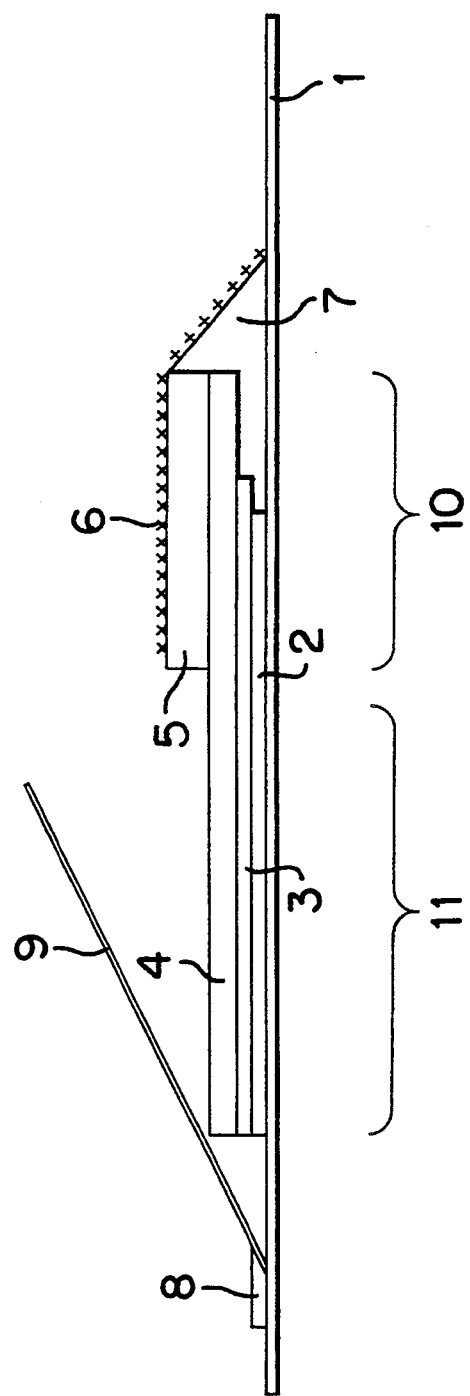
FIG. 1 shows a test apparatus useful in accordance with the invention.

The process according to the present invention for stabilizing NMHase is characterized in that the enzyme is treated with a nucleoside triphosphate, divalent metal ions and a complexing agent which complexes these metal ions.

In order to stabilize NMHase according to the present invention, divalent metal ions are first added to a solution which is preferably buffered and then a mixture of nucleoside triphosphate and enough complexing agent to complex all divalent metal ions which are present is added. As an alternative, first nucleoside triphosphate and then divalent metal ions complexed by a complexing agent can be added to the solution containing NMHase. Of course the NMHase can also be stabilized by the simultaneous addition of divalent metal ions, a complexing agent, which complexes the metal ions, and nucleoside triphosphate.

Nucleoside triphosphate is understood to include, e.g. ATP or GTP wherein ATP is particularly preferred. In order to stabilize NMHase in solution it is appropriate that the concentration of the nucleoside triphosphate is between 0.01 and 50 mmol/l, particularly preferably 0.1 to 20 mmol/l, especially preferably 1 to 15 mmol/l.

Ions are used as the divalent metal ions which act as cofactors for NMHase. The ions $Mg^{2+}$, $Mn^{2+}$ and $Zn^{2+}$ are preferred, $Mg^{2+}$ ions were particularly preferred. It is expedient to use them in the form of a salt which is soluble in an aqueous medium, for example as chlorides, sulphates etc., at a concentration between 0.1 and 10 mmol/l, especially preferably one between 0.5 and 5 mmol/l.

Multidentate ligands, cryptands, crown ethers etc. may be used as complexing agents of the aforementioned type which complex the divalent metal ions which are used and which can form stable chelate complexes with these in aqueous solutions. Multidentate ligands, in particular nitrilotriacetic acid, ethylenediamine tetraacetic acid, (EDTA), 1,2-cyclohexylene dinitrilotetraacetic acid, diethylene-triaminepentaacetic acid, 3-aza-3(carboxy-methyl) pentamethylene dinitrilotetraacetic acid, citric acid, ethylene bis-(oxyethylene-nitrilo)-tetraacetic acid and similar compounds have proven to be advantageous as such or in the form of salts which are soluble in an aqueous medium. Especially preferred are alkylenediamine acetic acids, in particular ethylenediamine tetraacetic acid (EDTA) or salts thereof. Cations which may be used for the complex-forming acids present in a salt form are basically all those which result in the formation of salts which are soluble in an aqueous medium and which in addition are not complexed by the complexing agents to the same extent as or stronger than the divalent metal ions which act as cofactors for NMHase. Alkaline metal ions are preferably used, particularly preferably $K^+$ ions.

According to the present invention a complexing agent for the stabilization of NMHase is used in such a concentration that all divalent metal ions acting as cofactors for NMHase are complexed by it. Hence the concentration of the complexing agent depends on the concentration of the divalent metal ions, the number of binding sites and the complex-formation constants of the complexing agent. The required concentration of the complexing agent can for example easily be determined by titration.

The enzyme is usually stabilized in an aqueous solution. The aqueous solution is preferably buffered for this, whereby the pH is between pH 7.0 and pH 9.0, preferably between pH 7.5 and 8.5. Substances which may be used to set the pH are those which have an adequate buffer capacity in the aforementioned range and which do not impair the activity of the enzyme, e.g. Tris, triethanolamine or TES [2-((Tris-hydroxymethyl)-methyl)) amino-ethane sulfonic acid]. TES buffer is particularly preferred. The concentration of the buffer is usually between 50 and 500 mmol/l, especially preferably between 100 and 300 mmol/l.

Usually between 0.01 and 40 U NMHase per ml buffer solution are used; in particular between 0.05 and 25 U, and preferably 0.10 to 20 U.

It is known from U.S. Pat. No. 4,816,393 that complexing agents such as EDTA are inhibitors of NMHase. Therefore it was surprising that enzyme-bound 1-methylhydantoin is completely degraded enzymatically to N-carbamoylsarcosine in the presence of a complexing agent, divalent metal ions and a nucleoside triphosphate although the divalent metal ions acting as cofactors are completely complexed by the complexing agent. The enzymatic degradation is continued in the presence of further enzymes which in turn degrade the N-carbamoylsarcosine which is formed such as e.g. N-carbamoylsarcosine amidohydrolase.

Furthermore it was very surprising that the NMHase enzyme which is no longer stabilized by substrate maintains its stability and enzymatic activity over a long period in the presence of the complexing agent and can thus be used advantageously for enzymatic methods of determination in which a stable NMHase is necessary.

In addition it was surprising that the nucleoside triphosphate used, in particular ATP, is no longer degraded by the ATPase side activity of NMHase after addition of the complexing agent and thus can be stored for a long time in a stable form in the presence of NMHase. This is all the more unexpected since statements can be found in the literature which indicate that EDTA has a stimulating effect on the enzyme ATPase (e.g. T. E. Barman, Enzyme Handbook, Vol. II, 1969, p. 689–690, Springer Verlag Berlin, Heidelberg, N. Y.

The NMHase stabilized according to the present invention can also be concentrated e.g. lyophilized. The NMHase also remains stable in a solid form.

The present invention also concerns a method for the determination of an analyte by means of a reaction catalyzed by NMHase which is characterized in that a NMHase stabilized according to the present invention is used.

Analyte is understood as a substance to be detected, in particular in body fluids such as blood, serum, plasma, urine, saliva etc., which can be converted to a substrate of NMHase by chemical or enzymatic reactions and thus can be determined by means of the NMHase reaction and subsequent detection of the reaction products. The analyte to be detected can also of course be NMH itself.

An example of such a method according to the present invention is a method for determining creatinine by converting creatinine to 1-methylhydantoin with creatinine deiminase, hydrolysing the latter with the 1-methylhydantoinase (NMHase) stabilized according to the present invention in the presence of nucleoside triphosphate and divalent metal ions which are preferably in excess over N-carbamoylsarcosine and nucleoside diphosphate and determining the N-carbamoylsarcosine which is characterized in that prior to carrying out the determination the NMHase is stabilized with a complexing agent which complexes the divalent metal ions which are used and at the beginning of the determination an excess of divalent metal ions is provided.

The invention can be used especially for the determination of creatinine in biological liquids from humans and animals, for example blood, plasma, serum, urine, saliva, or in liquid preparations of human or animal tissue. The invention can of course also be used for the determination of 1-methylhydantoin itself.

Methods of determining creatinine via 1-methylhydantoin and N-carbamoylsarcosine without the stabilization of the NMHase according to the present invention are known and the conditions stated for such methods and which are known to one skilled in the art are also suitable within the scope of the invention. They are for example described in U.S. Pat. No. 4,816,393.

In a preferred method for the determination of creatinine the N-carbamoylsarcosine which is formed after hydrolysis of 1-methylhydantoin is hydrolysed using N-carbamoylsarcosine amidohydrolase to form sarcosine. The known sarcosine oxidase reaction is particularly preferred for the detection of the sarcosine formed. Among the various detection reactions for the reaction products formed, as described for example in U.S. Pat. No. 4,816,393 it is the detection of the $H_2O_2$ formed in a colour reaction catalyzed by peroxidase by means of the oxidative coupling of 2,4,6 tribromo-2-hydroxybenzoic acid (TBHB) with 4-aminoantipyrine which is particularly preferred. This colour reaction can for example be measured photometrically. This reaction sequence is shown diagrammatically in the following:

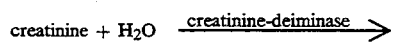
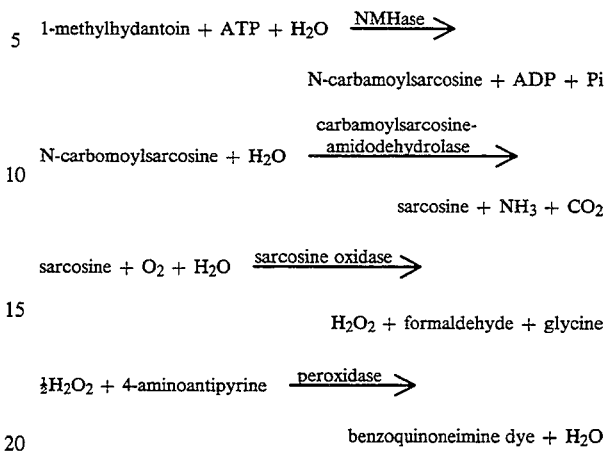

In order to carry out the creatinine determination according to the present invention the required enzymes and reagents are present in a solid or dissolved form.

The pH value of the aqueous solution for the analyte determination is usually between pH 7.0 and pH 9.0, preferably between pH 7.5 and pH 8.5. These pH conditions are especially suitable for the determination of creatinine. The buffer substances mentioned for stabilizing NMHase may, for example, be used to set the pH.

At the start of the measurement reaction, for example for the determination of creatinine, divalent metal ions are added to the reagent solution or to the reagent mixture, which contains the NMHase stabilized according to the present invention, in such an amount that the total concentration of metal ions exceeds that of the complexing agent i.e. so that there are sufficient divalent metal ions necessary for the NMHase reaction present in the mixture which are not complexed by the complexing agent. In this case the total concentration of divalent metal ions which are not complexed by the complexing agent is usually 0.1 to 30 mmol/l, particularly preferably between 0.5 and 15 mmol/l. The metal ions may be added together with the analyte to be determined or added shortly before or afterwards.

Particularly suitable divalent metal ions are $Mg^{2+}$, $Mn^{2+}$ and/or $Zn^{2+}$ ions, preferably $Mg^{2+}$ ions, in the form of their salts which are soluble in aqueous medium e.g. chlorides or sulphates.

In order to stabilize the NMHase according to the present invention nucleoside triphosphate is added. If this amount of nucleoside triphosphate is not sufficient when using the NMHase stabilized according to the present invention to convert the NMH formed during the course of the analyte determination, then proportionately more nucleoside triphosphate must be used in the determination method.

It is expedient that the final total concentration of nucleoside triphosphate for the determination reaction, in particular of ATP and/or GTP, is between 0.01 mmol/l. and 50 mmol/l, preferably between 0.1 mmol/l and 20 mmol/l, especially preferably between 1 mmol/l and 15 mmol/l.

Usually between 0.01 U and 40 U NMHase are used per ml reaction mixture, in particular between 0.05 U and 25 U, preferably 0.10 to 20 U.

The addition of potassium and/or ammonium salts, in particular ammonium salts, has proven to be advantageous in increasing the activity of NMHase. In this case salts are understood as those which are soluble in aqueous medium. The total final concentration of these is preferably between 0.1 mmol/l and 100 mmol/l, particularly preferably between 5 mmol/l and 10 mmol/l.

The concentrations of the other enzymes and reagents necessary for the creatinine test can be derived from U.S. Pat. No. 4,816,393. Representative values are also quoted in the examples of the present application.

Generally, the upper concentration limits for the enzymes and reagents are determined by their solubility and by economical considerations. The lower limits are determined by the necessary sensitivity of the determination reaction.

A stabilized NMHase composition according to the present invention enables an advantageous enzymatic determination method, in particular a method for determining creatinine, wherein 1-methylhydantoin is converted and a prerequisite is a stable NMHase and stable nucleoside triphosphate without which enzyme-bound 1-methylhydantoin (or a substrate analogue) influences this determination method by a blank reaction.

In a preferred method the stabilized NMHase according to the present invention is brought into contact with those enzymes which are necessary for the determination reaction before the measurement reaction is started and before admixing the $H_2O_2$ indicator in order to eliminate a blank reaction caused by enzyme-bound NMH in a determination method according to the present invention. These include the enzymes N-carbamoylsarcosine amidohydrolase, sarcosine oxidase and if necessary peroxidase. These and many other commercial enzymes contain traces of the $H_2O_2$-degrading enzyme catalase. It can also be added separately if necessary. The $H_2O_2$ formed during the enzymatic degradation of the NMH bound to NMHase according to the above reaction scheme is thus removed by catalase in a reaction prior to the actual measurement reaction without the slowly reacting catalase interfering with the indicator reaction during the later measurement reaction.

The present invention also concerns a reagent containing 1-methylhydantoinase for carrying out the method according to the present invention described above for the determination of an analyte via a reaction catalyzed by 1-methylhydantoinase which is characterized in that it contains divalent metal ions, nucleoside triphosphate and a complexing agent which complexes these metal ions.

A reagent for the detection of an analyte, such as creatinine, which contains NMHase, is characterized in that it contains one or several enzymes and substances which convert the analyte to be determined into NMM. Creatinine deiminase has proven to be advantageous for the determination of creatinine. In addition the reagent according to the present invention contains divalent metal ions, a nucleoside triphosphate, such as ATP or GTP, a complexing agent which complexes the metal ions, a buffer substance for setting the pH at a value between pH 7.0 and pH 9.0 as well as a system for detecting N-carbamoylsarcosine. This system preferably contains the enzymes N-carbamoylsarcosine amidohydrolase and sarcosine oxidase.

This detection system can also contain an agent for the determination of $H_2O_2$. This system and other systems for detecting the reaction products of the decomposition of N-carbamoylsarcosine are known, e.g. from H. U. Bergmeyer, Methoden der enzymat. Analyse, Verlag Chemie, Weinheim.

In addition the reagent according to the present invention can also contain, if desired, additional $K^+$ ions or $NH_4^+$ ions, preferably $NH_4^+$ ions, in the form of corresponding water-soluble salts.

In addition to the aforementioned constituents, the reagent according to the present invention can also contain auxiliary substances such as wetting agents, lipases, builders, stabilizers etc.

Further possible reagent constituents as well as possible concentration ranges for the reagent components according to the present invention correspond to those mentioned above for carrying out the method according to the present invention for the determination of an analyte.

The reagent according to the present invention can be present as a solution. In this case the necessary reagent components can be present together in an aqueous solution. Preferably, however, they are distributed among several solutions. Thus the invention also concerns a reagent kit for the determination of an analyte by means of a reaction catalyzed by 1-methylhydantoinase (NMHase). The kit according to the present invention comprises at least two containers one of which contains the stabilized NMHase according to the present invention and a second container which contains the divalent metal ions as well as, if desired, $K^+$ ions and/or $NH_4$ ions. It is especially preferred that the first container also contains the other enzymes necessary for the determination reaction and that the second container in addition contains the dye necessary for the indicator reaction. The components can be present dissolved in the form of an aqueous solution or they can be present in a solid form, for example as a lyophilisate, and are dissolved before use. Such a reagent kit is particularly useful for incubating the sample with the NMHase preparation in the first container mentioned above and then to start the determination reaction by the addition of divalent metal ions from the second container or for combining the sample to be examined for analyte with divalent metal ions from container 2 and to start the determination reaction by addition of the enzyme preparation from container 1.

The method of determining analytes such as creatinine according to the present invention can also be carried out using a so-called dry test. In this case the reagent according to the present invention is bound to a carrier. Devices which are suitable for carrying out a dry test are known to one skilled in the art, for example from U.S. Pat. Nos. 4,321,834, 4,820,489, 4,816,076 and European Patent Application EPA 309883. They are usually denoted test carriers or test strips. In this case the reagent necessary for carrying out a test are present in a dry form, i.e. not dissolved in a liquid, for example in or on absorptive materials such as paper, an open film according to U.S. Pat. No. 4,321,834 a glass fibre pad or a porous plastic membrane to mention only a few of the possible materials, or in or on a material capable of swelling such as e.g. an appropriate plastic film, gelatin or cellulose.

When the sample liquid to be tested is applied to the test carrier or the test carrier is immersed in the sample liquid a liquid medium forms in the test carrier within which the test reaction proceeds. The colour formation caused by the reaction can be evaluated visually or photometrically e.g. by reflectance photometry. In order to manufacture the reagent according to the present invention in a carrier-bound form, a suitable carrier material such as filter paper, cellulose or plastic fibre pad is impregnated with solutions of the reagent necessary for the manufacture of test carriers in readily volatile solvents such as water or ethanol. This can be carried out in an impregnation step in which solutions are used which each contain some of the constituents of the final reagent. The carrier material treated in this way can be used as such or be glued to handles or to stiff plastic foils in a known manner. The substances necessary for the determination reaction can, however, also be applied on or in the carrier material using in each case separate solutions in separate impregnation operations.

Instead of multiple impregnation of the same carrier material, the constituents of the reagent according to the present invention can also be distributed on different carrier materials which are brought into contact with one another in such a manner that an exchange of liquid is possible during the determination of the analyte. It is expedient to carry out the determination of an analyte by means of a NMHasecatalysed reaction using a multilayered test carrier. In this case the divalent metal ions, a nucleoside triphosphate such as ATP or GTP and the complexing agent which complexes the metal ions which are necessary to stabilize the NMHase according to the present invention are applied together with NMHase and the enzymes necessary for the test reaction to a carrier material which is in the form of a layer and the additional amount of divalent metal ions necessary for starting the test, which altogether produces an excess of metal ions compared to the complexing agent used, are applied to a further layer of the same or another carrier material. In this case both layers should be in a contact which enables exchange of liquid or should be able to be brought into such a contact.

In a particular preferred embodiment of the test carrier the $K^+$ ions or ammonium ions which are advantageous for increasing the NMHase activity and the chromophoric indicator system are also located on the layer which contains the additional amount of divalent metal ions.

The final total concentration of the individual enzymes and reagents on the test carrier during the test procedure are preferably at the upper end of the concentration ranges stated above for a determination method in solution.

An especially preferred embodiment of a test carrier according to the present invention is shown in cross-section in FIG. 1. A base foil (1) serves as a supporting layer for several liquid-absorbing layers which lie flat. One or several layers (2) containing enzymes, if desired an indicator layer (3) and a transport pad (4) are mounted in this sequence on top of one another on the base foil (1). They are in contact with one another in such a way as to enable an exchange of liquid. The transport pad completely covers the area of the layers (2) and (3). The two longitudinal ends of this pile of layers are denoted application zone (10) or detection zone (11). An erythrocyte separation layer (5) is mounted on that part of the transport pad (4) which is denoted application zone (10) and is covered by a cover net (6) to protect it from damage. The transport pad (4) as well as the erythrocyte separation layer and the cover net (6) and also the layers (2) and (3) are attached at the end located in the application zone (10) to the base (1) by means of a hot-melting adhesive strip (7).

A transparent flap (9) is fastened to the base foil (1) with a drop of hot-melting adhesive (8) in such a way that it can be brought into contact with the part of the transport pad which is in the detection area by means of an external manipulation e.g. pressure. The purpose of the flap (9) is to accelerate the exchange of liquid within the layers (2), (3) and (4) by means of pressure.

It consists of a foil, preferably of a plastic which is transparent to visible light. A polycarbonate foil is particularly preferred for this.

The transport pad (4) can be selected from a multitude of materials. Particularly suitable are papers, fleeces and those film layers which have a considerable absorptive capacity for liquids due to an open structure with many capillary gaps. This absorptive capacity must be high enough to ensure that the amount of liquid which is then absorbed is sufficient to completely wet all reagent layers necessary for the test reaction. Glass fibres are particularly preferred. Glass fibres are also particularly preferred for the erythrocyte separation layer (5) (cf. U.S. Pat. No. 4,816,224).

The layers (2) or (3) are usually composed of materials with absorptive properties which are impregnated with the respective reagents (enzymes or indicators and possibly other necessary substances). Plastic or natural materials are suitable for this.

Preferred potential plastic materials are polyamide fabrics and polyester fabrics are especially preferred.

Preferred natural materials are especially paper, and quite especially tea bag paper such as e.g. that having a weight of about 10–20 g/m², preferably 12 g/m² made from Manila long-fibre hemp.

In order to carry out the analysis 30 µl blood is for example applied to the cover net (6) and the erythrocyte separation layer (5). The sample seeps into the transport layer (4) which is underneath and into the layers (2) and (3), whereby the erythrocytes are separated. The plasma formed in this way is transported in the layers (2), (3) and (4) in the longitudinal direction of the test carrier into the detection region (11). In this process a reaction takes place in these layers between the constituents of the sample which is to be determined and the reagents impregnated on the layers (2) and (3).

At a certain time after applying the sample the indicator reaction is for example determined photometrically (for example by Reflotron ®, Boehringer Mannheim GmbH, Mannheim, German Federal Republic) after pressing down the transparent flap (9).

The invention is described in more detail in the following examples.

EXAMPLE 1

Manufacture of reagent carriers for the detection of creatinine with a stabilized NMHase according to the present invention and with NMHase according to the state of the art.

a) Reagent carrier with NMHase after prior degradation of enzyme-bound NMH (stabilized NMHase according to the present invention).

A test carrier is manufactured according to FIG. 1. The enzyme paper (2) is manufactured by dissolving 250 mmol/l TES
12 mmol/l EDTA
50 mmol/l ATP
1.5 mmol/l $MgCl_2$ while adjusting the pH value with potassium hydroxide solution, the final pH is 8.4. The following are dissolved successively into this while stirring:

150 g/l sucrose
45 kU/l NMHase (from Arthrobacter spec.)
450 kU/l creatinine deiminase (Crimi)
186 kU/l N-carbamoylsarcosine amidohydrolase (CSHase)
150 kU/l sarcosine oxidase (Sarc-OD)
7800 kU/l peroxidase (POD)
150 kU/l ascorbate oxidase (AAO)

The enzymatically bound NMH of the NMHase is degraded in this solution within 10 minutes.

The ready-to-use impregnation solution is applied to an absorptive paper (long-fibre paper, Schoeller, Germsbach, German Federal Republic, weight: 12 g/m$^2$) or the paper is immersed in the impregnation solution. Subsequently it is dried for 5 min at 50° C. This results in an enzyme paper (2) with the following constituents:

3.4 g/m$^2$ TES
0.27 g/m$^2$ EDTA
2.1 g/m$^2$ ATP
0.02 g/m$^2$ MgCl$_2$ ×6H$_2$O
9 g/m$^2$ sucrose
2.8 1 kU/m$^2$ NMHase
28 kU/m$^2$ Crimi
12 kU/m$^2$ CSHase
9 kU/m$^2$ Sarc-0D
474 kU/m$^2$ POD
9 kU/m$^2$ AAO The indicator paper (3) is manufactured in an analogous manner and this contains the following constituents after the impregnation:

0.4 g/m$^2$ 2-( 3,5-di-tert-butyl-hydroxyphenyl)-4-(5)-(9-Julolidino)-5-(4 )-methyl-(1H) imidazole. HCl (see U.S. Pat. No. 4,665,023)
3 g/m$^2$ Synperonic ® F 68(polyethyleneglycol-polypropyleneglycol copolymer;Serva, Heidelberg, German Federal Republic)
0.8 g/m$^2$ NH$_4$Cl
0.3 g/m$^2$ MgCl$_2$.

The test carrier is manufactured by mounting the enzyme paper (2) (12 mm×6 mm), the indicator paper (3) (13 mm×6 mm), a 16 mm long, 6 mm wide and 0.25 mm thick glass fibre pad with a weight of 25 g/m$^2$ as the transport pad (4), a 6 mm wide, 6 mm long and 700 μm thick glass fibre pad with a weight of 60 g/m$^2$ as the erythrocyte separation pad (5) and a protecting net (6) made of Scrynel PE28OHC red ® (polyethylene, Zuricher Beuteltuchfabrik AG, Rüschlikon, Switzerland) measuring 6×8 mm and having a mesh size of 200 μm in this order on a 500 μm thick, 10 cm long and 6 mm wide polyester foil (ICI Company, Frankfurt, German Federal Republic) (1) by means of a hot-melting adhesive strip (7) as shown in FIG. 1.

A 200 μmm thick, 15 mm long and 6 mm wide transparent polycarbonate foil (Pokalon ®, Lonza, Rheinfelden, German Federal Republic) (9) is mounted as a flap on the carrier foil (1) by means of a drop of hot-melting adhesive (8) in such a way that it can be pressed onto the transport pad (4) by means of pressure.

The NMHase in the enzyme paper is stable so that this test carrier can be stored for at least 1 year at room temperature without noticeable losses in enzyme activity.

Figure 2:
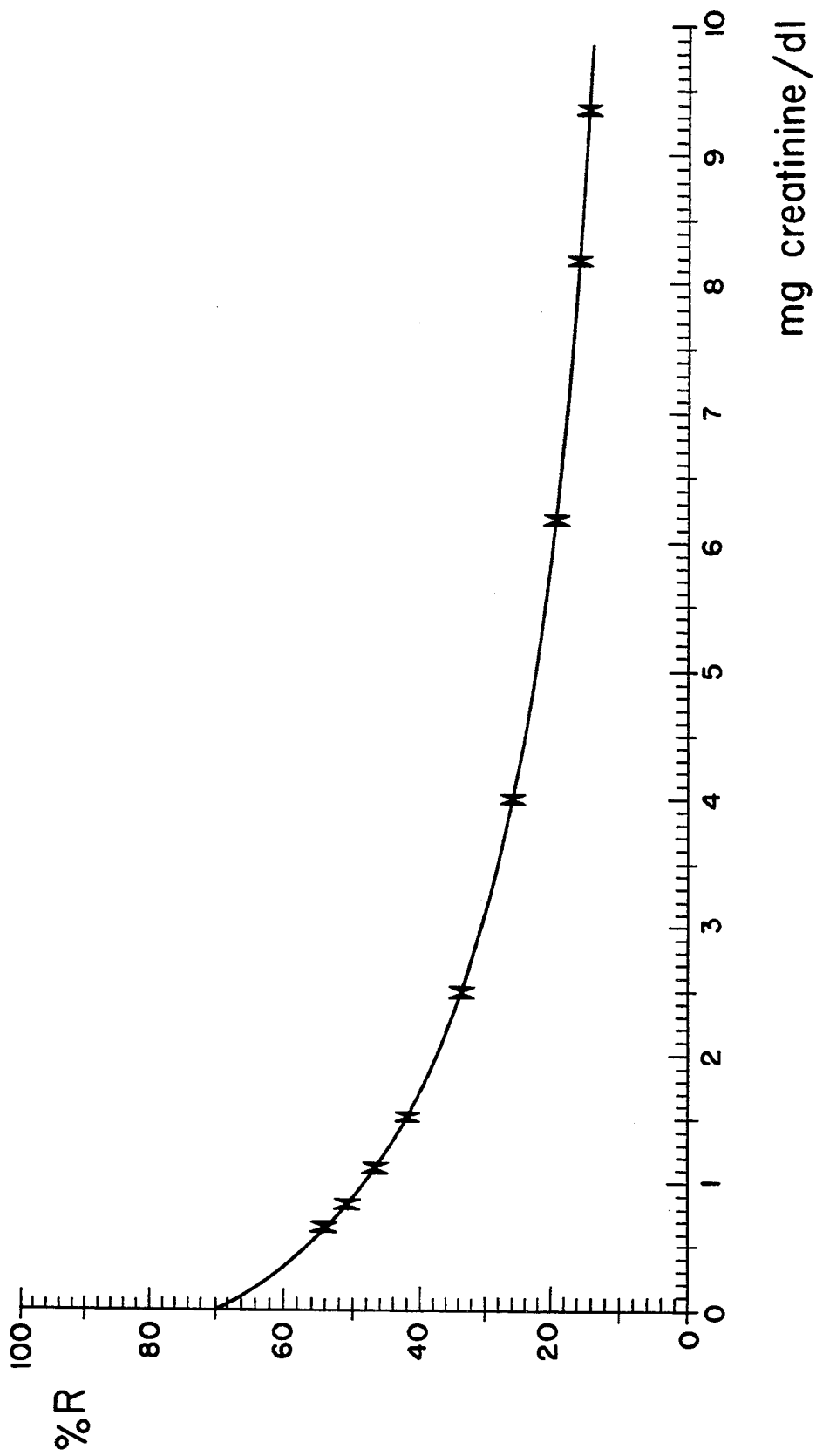
FIG. 2 shows a calibration curve obtained using known creatinine concentrations.

For creatinine determination a 30 μl sample (e.g. blood) containing creatinine is applied to the protecting net (6). After 30 sec. pressure is applied to the transparent foil (9) which is pressed onto the transport pad (4), the liquid contained therein and the underlying indicator and enzyme paper (3) and (2). After a further 60 sec. the reflectance in percent is measured through the transparent foil (9) at 642 nm in a suitable reflectance photometer (e.g. Reflotron ®, Boehringer Mannheim GmbH, Mannheim, German Federal Republic). A calibration curve with known creatinine concentrations serves to determine the unknown concentrations (FIG. 2).

b) Reagent carrier with NMHase without the degradation of enzyme-bound NMH according to the present invention.

An impregnation solution for the enzyme paper is prepared according to Example 1a, but which is absolutely free of Mg$^{2+}$ions. A test carrier analogous to Example 1a is manufactured with Mg$^{2+}$-free enzyme paper.

EXAMPLE 2

Measurement of the blank signal of the reagent carrier according to Example 1a (test carrier according to the present invention) and according to Example 1b (test carrier according to the state of the art). 30 μof a 6% bovine serum albumin solution which contains neither creatinine nor NMH is applied to a reagent carrier according to Example 1a (containing no enzyme-bound NMH) and according to Example 1b (still containing enzyme-bound NMH) and the dependence of the change in reflectance signal on time is recorded. Seconds Reagent carrier Reagent carrier

| Seconds | Reagent carrier of Example 1a Reflectance % | Reagent carrier of Example 1b Reflectance % |
| --- | --- | --- |
| 0 | 69.8 | 70.0 |
| 12 | 69.9 | 56.1 |
| 24 | 69.9 | 51.8 |
| 36 | 69.9 | 50.0 |
| 48 | 70.0 | 50.5 |
| 60 | 70.0 | 50.8 |

A stable measurement signal is established after 60 sec. The reflectance signal remains almost unchanged using the reagent carrier according to Example 1a while the reagent carrier according to Example 1b shows a significant reaction due to the degradation of enzyme-bound NMH. This blank signal simulates a concentration of 0.07 mmol/l creatinine in serum. At a lower limit of the measurement range for creatinine in serum of ca. 0.04 mmol/l such a signal leads to a considerable error in the creatinine determination.

Similar stable measurement signals are obtained with test carriers according to Example 1a, whereby, for the stabiliszation of NMHase, EDTA is replaced by different other complexing agents.

| Complexing agent | Reflectance after ... seconds | | | | | |
| --- | --- | --- | --- | --- | --- | --- |
| | 0 | 12 | 24 | 36 | 48 | 60 |
| nitrilo triacetic acid | 70.1 | 69.8 | 69.6 | 69.4 | 69.3 | 69.3 |
| 1,2-cyclohexane diamine-N,N,N,N'-tetraacetic acid | 69.5 | 69.2 | 69.0 | 69.0 | 68.9 | 69.0 |
| 3-aza-3-(carboxymethyl)-pentamethylene nitrilo tetraacetic acid | 70.4 | 70.1 | 69.9 | 69.9 | 69.9 | 69.9 |
| ethyleneglycol-bis-(β-amino ethylether) N,N-tetraacetic acid | 70.3 | 70.7 | 70.6 | 70.5 | 70.5 | 70.5 |
| citrate | 70.0 | 69.8 | 69.7 | 69.6 | 69.5 | 69.5 |

| Complexing agent | Reflectance after ... seconds | | | | | |
|---|---|---|---|---|---|---|
| | 0 | 12 | 24 | 36 | 48 | 60 |
| oxalate | 69.8 | 69.5 | 69.3 | 69.3 | 69.2 | 69.2 |

EXAMPLE 3

Stability of NMHase
a) without enzyme-bound NMH
b) with enzyme-bound NMH in the presence of $Mg^{2+}$ ions and ATP
c) after stabilization according to the present invention with EDTA, $Mg^{2+}$ ions and ATP.

Impregnation solutions for the enzyme papers were prepared according to Example 1a.
a) 45 U/ml NMHase without enzyme-bound NMH without EDTA and $MgCl_2$
b) 45 U/ml NMHase with enzyme-bound NMH without EDTA and $MgCl_2$
c) 45 U/ml NMHase with enzyme-bound NMH impregnation solution according to the present invention with EDTA and $MgCl_2$ A time course of the enzyme activity of the NMHase in the three impregnation solutions was determined according to EP-A-0 154 269.

| Time (h) | NMHase without enzyme-bound NMH, without EDTA and $MgCl_2$ | NMHase with enzyme-bound NMH without EDTA and $MgCl_2$ | NMHase with enzyme-bound NMH in impregnation solution according to the present invention |
|---|---|---|---|
| 0 | 100% | 100% | 100% |
| 0.5 | 65 | 93 | 94.7 |
| 1 | 37 | 93 | 94.5 |
| 2 | 15 | 95 | — |
| 4 | 7 | 97 | 106 |
| 6 | 1 | 90 | — |
| 24 | 0 | 76 | 97 |

According to this the NMHase without enzyme-bound NMH shows a marked instability which makes it no longer processable. In contrast the NMHase with enzyme-bound NMH is stable, but shows a blank reaction in Example 1b. In contrast the NMHase treated according to the present invention shows an excellent stability although it no longer contains any enzyme-bound NMH.

EXAMPLE 4

Stability of ATP in the presence of
a) stabilized NMHase according to the present invention
b) NMHase without EDTA treatment Two enzyme impregnation solutions are prepared according to Example 1a
a) with EDTA
b) without EDTA
and the time course of the ATP concentration is measured.

| Time (h) | Impregnation solution with EDTA | Impregnation solution without EDTA |
|---|---|---|
| 0 | 100% | 100% |
| 1.5 | 95.1 | 33 |
| 4 | 90.9 | 5 |
| 24 | 87.9 | >1 |

ATP in the impregnation solution according to the present invention a) remains adequately stable whereas it is degraded within a short time period in the impregnation solution b) without EDTA.

The following values indicate the concentration of ATP (in %) after 24 h in impregnation solutions, in which EDTA is replaced by different other complexing agents. (ATP concentration at the beginning: 100%).

| Complexing agent | concentration of ATP in % after 24 h |
|---|---|
| nitrilo triacetic acid | 72.6 |
| 1,2-cyclohexane diamine-N,N,N,N'-tetraacetic acid | 81.7 |
| 3-aza-3-(carboxymethyl)-pentamethylene nitrilo tetraacetic acid | 91.7 |
| ethyleneglycol-bis-($\beta$-amino ethylether)-N,N-tetraacetic acid | 66.5 |
| citrate | 62.3 |
| oxalate | 57.3 |

All complexing agents effect an adequate stability of ATP.

We claim:
1. Process for stabilizing 1-methylhydantoinase (NMHase) comprising adding to a sample which contains NMHase but which also does not contain any free 1-methylhydantoin:
   (i) a divalent metal ion,
   (ii) a nucleoside triphosphate, and
   (iii) a complexing agent in an amount sufficient to complex said divalent ion.
2. Process of claim 1, wherein said divalent metal ion is $Mg^{2+}$, $Mn^{2+}$ or $Zn^{2+}$.
3. Process of claim 1, wherein said complexing agent is ethylenediamine tetraacetic acid or a salt thereof.
4. Process of claim 1, wherein said nucleotide triphosphate is adenosine triphosphate.
5. Stabilized reagent for determining an analyte involved in a 1-methylhydantoinase (NMHase) catalyzed reaction, comprising:
   (i) NMHase which has no 1-methylhydantoin bound to it,
   (ii) a divalent metal ion,
   (iii) a nucleoside triphosphate, and
   (iv) a complexing agent present in an amount sufficient to complex said divalent metal ion.

6. Reagent of claim 5, further comprising a source of K+ ions or a source of NH4+ ions.

7. Reagent of claim 5, further comprising a system useful in detecting N-carbamoylsarcosine and a buffer, wherein said reagent has a pH from 7.0 to 9.0.

8. Reagent of claim 7, wherein said system comprises:
   (v) N-carbamoylsarcosine amidohydrolase,
   (vi) sarcosine oxidase,
   (vii) peroxidase, and
   (viii) an $H_2O_2$ detection reagent.

9. Reagent of claim 8, further comprising (ix) a catalase.

10. Reagent of claim 5, wherein said reagent is impregnated on a solid carrier.

11. Method for determining an analyte in a sample, comprising:
   (i) reacting said analyte with a substance to generate 1-methylhydantoin,
   (ii) adding the reagent of claim 5 to said sample,
   (iii) adding an amount of a divalent metal ion which, when combined with divalent metal ion in said reagent yields a total in excess relative to the complexing agent in said reagent, and
   (iv) determining N-carbamoylsarcosine in said sample as a measure of said analyte.

12. Method of claim 11, further comprising adding K+ or NH4+ to said sample.

13. Method of claim 11, further comprising adding N-carbamoylsarcosine amidohydrolase and sarcosine oxidase to determine N-carbamoyl sarcosine.

14. Reagent kit for determination of an analyte, comprising:
   (i) a first container which contains NMHase, a divalent metal ion, a nucleoside triphosphate and a complexing agent present in an amount sufficient to complex the divalent metal ion in said first container, and
   (ii) a second container which contains a divalent metal ion in an amount which, when combined with the divalent metal ion in said first container, is in excess relative to said complexing agent.

15. Reagent kit of claim 14, wherein at least one of said first and second containers further comprise K+ or NH4+.

16. Reagent kit of claim 14, wherein said first container contains N-carbamoylsarcosine amidohydrolase and sarcosine oxidase, and said second container further comprises an $H_2O_2$ detection agent.

17. Reagent kit of claim 16, wherein said first container further comprises peroxidase.

18. Reagent of claim 16, wherein said first container also contains catalase.

* * * * *